(12) United States Patent  
Allgeyer

(10) Patent No.: US 7,610,085 B2
(45) Date of Patent: Oct. 27, 2009

(54) SIMPLIFIED ECG MONITORING SYSTEM

(76) Inventor: Dean O. Allgeyer, 762 Glenmont Ave., Los Angeles, CA (US) 90024

( * ) Notice: Subject to any disclaimer, the term of this patent is extended or adjusted under 35 U.S.C. 154(b) by 107 days.

(21) Appl. No.: 11/519,520

(22) Filed: Sep. 12, 2006

(65) Prior Publication Data

US 2008/0077027 A1    Mar. 27, 2008

(51) Int. Cl.
    *A61B 5/00*    (2006.01)
(52) U.S. Cl. ............................. 600/513; 600/483
(58) Field of Classification Search ................. 600/323, 600/325, 483, 502, 503, 509, 513, 523, 525
    See application file for complete search history.

(56) References Cited

U.S. PATENT DOCUMENTS

| 4,751,931 | A | * | 6/1988 | Briller et al. ............... 600/513 |
| 4,920,969 | A | * | 5/1990 | Suzuki et al. ............... 600/436 |
| 4,960,126 | A | * | 10/1990 | Conlon et al. ............... 600/336 |
| 5,224,479 | A | * | 7/1993 | Sekine ........................ 600/389 |
| 5,511,546 | A | * | 4/1996 | Hon ............................ 600/490 |
| 5,931,791 | A | * | 8/1999 | Saltzstein et al. ........... 600/513 |
| 6,516,289 | B2 | * | 2/2003 | David ......................... 600/384 |
| 6,662,032 | B1 | * | 12/2003 | Gavish et al. ............... 600/323 |
| 6,842,722 | B2 | * | 1/2005 | David ......................... 702/189 |
| 6,858,012 | B2 | * | 2/2005 | Burns et al. ................ 600/483 |
| 7,277,743 | B2 | * | 10/2007 | Brodnick ..................... 600/382 |
| 7,300,404 | B1 | * | 11/2007 | Kolluri et al. ............... 600/493 |
| 7,305,262 | B2 | * | 12/2007 | Brodnick et al. ............ 600/324 |
| 2002/0077536 | A1 | * | 6/2002 | Diab et al. .................. 600/323 |
| 2003/0120164 | A1 | * | 6/2003 | Nielsen et al. .............. 600/513 |
| 2003/0216651 | A1 | * | 11/2003 | Burns et al. ................ 600/483 |
| 2004/0073127 | A1 | * | 4/2004 | Istvan et al. ................ 600/513 |
| 2005/0113703 | A1 | * | 5/2005 | Farringdon et al. ......... 600/509 |

OTHER PUBLICATIONS

Goldberger, Emanuel. "A Simple, Indifferent, Electrocardiographic Electrode of Zero Potential and a Technique of Obtaining Augmented, Unipolar, Extremity Leads". American Heart Journal, Apr. 1942. vol. 23 issue 4, pp. 483-492.*

* cited by examiner

*Primary Examiner*—Carl H Layno
*Assistant Examiner*—Gary A Porter, Jr.
(74) *Attorney, Agent, or Firm*—Samuel L. Alberstadt

(57) ABSTRACT

A simplified device and method for continuous ECG monitoring incorporates electrodes in a pulse oximeter finger probe and/or in a blood pressure cuff. The electrodes in the pulse oximeter and blood pressure cuff generate a continuous ECG tracing without the use of disposable electrodes connected to multiple electrical wires in an ECG harness. In another embodiment, simplified ECG monitoring system can act as a secondary ECG input to a system that uses a primary ECG input as well.

16 Claims, 3 Drawing Sheets

A # SIMPLIFIED ECG MONITORING SYSTEM

FIELD OF THE INVENTION

This invention relates to electrocardiograph (ECG) monitoring of patients. By placing ECG electrodes in a pulse oximeter probe and in a blood pressure cuff, an ECG tracing can be generated without the use of an ECG wire harness and disposable electrodes.

BACKGROUND OF THE INVENTION

Modern medical practice mandates certain monitoring standards for patients, depending on the acuteness of a patient's condition. For example, blood pressure (BP), pulse oximetry, and electrocardiography are standard monitors for most patients, whether in hospitals, outpatient facilities, nursing homes, or even in a significant number of home care situations. Pulse oximetry relies on pulsatile arterial flow to generate a signal, which is analyzed to determine hemoglobin oxygenation. Pulse oximeters are typically finger-mounted, spring loaded devices with wires connected to some type of display. Automated, non-invasive blood pressure determination utilizes the oscillometric method of blood pressure calculation. This technique inflates a blood pressure cuff above vascular occlusion pressure, which causes a cessation of blood flow and consequently prevents the generation of a signal for pulse oximeter analysis. As a result of this monitoring conflict, the BP cuff and the pulse oximeter are almost invariably placed on opposite arms, so that an inflated BP cuff does not interfere with the blood flow used for oxygen saturation monitoring.

The electrocardiograph is also a basic tool of patient monitoring. Cardiac variables such as rate and rhythm are provided through a system of wires and disposable skin electrodes, which transmit the cardiac depolarization voltage waveforms to a display, such as a modified oscilloscope, or printer, or both, where the waveform is displayed to the medical practitioner. Typically, such a visible waveform, whether displayed by an electronic device or printed on paper, is called an ECG tracing.

In prior art ECGs, a system of wires and disposable skin electrodes constitute electrical connections from the patient to a variety of well known signal processing and display devices. The wires are often grouped together into a harness. The wires and electrodes are configured in standardized arrangements known to those of skill in the art. A signal is generated using two active electrodes. A third, inactive electrode ordinarily serves as a ground. Two active electrodes are often referred to as a "lead." The electrodes have standardized polarities, and they are usually placed at standardized body locations. These standardized locations create standardized leads which are known to those of skill in the art. For example, FIG. 1 depicts a prior art ECG monitoring system with several wires and skin electrodes. A standardized "lead 1" is defined by two active electrodes placed on the right and left arms. The left arm is by convention defined as the positive electrode. A ground electrode is placed on the left chest wall. Each of the disposable electrodes is connected to a separate wire that is connected to a wire hub M. The left arm-right arm configuration—a "lead 1"—results in a generally positive ECG waveform, as the major cardiac depolarization vector travels from right to left and downward. Other, different electrode locations on the body produce additional, well known leads, each with its own associated waveform.

Variations of ECG monitoring systems and methods exist, depending on the amount of patient information the practitioner desires. For example, a twelve lead ECG is considered by many to represent the standard for a complete assessment of cardiac function, because it provides a substantial amount of information for numerous cardiac conditions. The conditions of most patients do not call for such complex and intense monitoring.

The most typical ECG monitoring setup employs a three-electrode, three-wire system that generates an ECG waveform or tracing. This monitoring setup is encountered in the emergency room, preoperative area, operating room, postoperative area, and frequently in the intensive care unit as well. The medical practitioner typically uses this monitoring setup, because he is primarily or exclusively interested in the patient's heart rate and rhythm. If the practitioner's only interest is in the heart's rate and rhythm, additional wires, and electrodes are superfluous. A three electrode system containing two active electrodes and one ground can generate an ECG tracing sufficient to provide the practitioner with the information he deems necessary.

There are many instances when a single lead (i.e., three electrode) ECG tracing or waveform, combined with oxygen saturation level and blood pressure, provides sufficient patient monitoring information. One instance includes what are known as minor procedures. For example, a patient who has undergone an uneventful cataract removal or a colonoscopy is monitored in the recovery room with a BP cuff, pulse oximetry, and a single lead ECG tracing. Under such circumstances, a more complex system of monitoring is unnecessary. It can also be detrimental. Excessive complexity is physically cumbersome, unnecessarily costly, wastes the practitioner's time, and slows treatment of multiple patients or else requires more human resources to do so. Whether the desired ECG is simple or complex, many types of "vital signs" monitors incorporate ECG, pulse oximetry, and automated blood pressure determination and display within a single unit. Most of these monitors include the multiple wires depicted in FIG. 1. In addition, they also include connections (not shown) from pulse oximeters and blood pressure cuffs.

In prior art monitoring devices, the multiplicity of wires is often referred to derogatively as spaghetti, as the wires tangle or often interfere with other medical hardware and the activities of medical personnel who are treating or attending to the patient. This arrangement increases the likelihood of the disposable electrodes being dislodged from the patient's body. All of these problems unnecessarily increase the use and cost of technical and human medical resources. In many instances, reducing spaghetti and its associated problems is desirable as long as pertinent patient data is not sacrificed. Though the time required for any single patient's ECG harness to be attached and detached may seem insignificant, in aggregate, given the tens of millions of such procedures annually and the premium placed on the efficiency of medical personnel, eliminating the time and problems associated with a multiple wire harness would be substantial.

Various prior art devices and techniques reduce clutter and organize the medical environment. For example, Glass, in U.S. Pat. No. 6,536,699, details the problem of wire and cord entanglement and provides a solution for organization. Webb, in U.S. Pat. No. 5,974,708, provides a solution for organizing intravenous lines. Therefore, it is desirable to provide a patient monitoring device and method that provide a continuous ECG tracing without the use of a multiplicity of wires.

SUMMARY OF THE INVENTION

The present invention can provide an ECG tracing without the use of a harness, numerous unnecessary wires, and disposable electrodes. The present invention preferably embeds dry, reusable electrodes within a pulse oximeter probe and a blood pressure cuff. By embedding ECG electrodes within the pulse oximeter probe and BP cuff and connecting them to the display terminal, an ECG waveform can be displayed and observed by the medical practitioner. This arrangement provides the rate and rhythm information provided by a lead 1 of a prior art ECG monitoring system. Preferably, the input from this system is automatically and dynamically configured to define the left arm as the positive electrode consistent with the standard polarity arrangement. In addition, by connecting the pulse oximeter and BP cuff to the monitoring system, the medical practitioner can simultaneously obtain the patient's oxygen saturation level and blood pressure along with the ECG reading.

In one embodiment, the invention includes an electrical connection operatively connected to an ECG tracing display and to at least one of a pulse oximeter and a blood pressure cuff. It also includes an electrode configured to be in operative connection with the at least one of a pulse oximeter and/or blood pressure cuff and in operative connection with the patient.

In another embodiment of the invention, a system for monitoring a patient's oxygen saturation level, blood pressure, and cardiac function, includes an ECG display; a blood pressure cuff connected to a blood pressure display; a pulse oximeter connected to an oxygen saturation display; an ECG electrode operatively connected to the pulse oximeter; and an electrical connection between the ECG electrode and the ECG display.

In another embodiment, a method for displaying a patient's ECG tracing, blood pressure, and oxygen saturation level includes attaching to the patient a pulse oximeter having at least one ECG electrode, the pulse oximeter and the ECG electrode each operatively connected to a display; attaching to the patient a blood pressure cuff, the blood pressure cuff operatively connected to the display; and displaying the patient's ECG, oxygen saturation level, and blood pressure.

In one of the preferred embodiments of the invention, the pulse oximeter includes an active and ground ECG electrode, and the blood pressure cuff includes another active ECG electrode. The electrodes are preferably reusable without replacement. These non-disposable electrodes can be made of Ag/AgCl, which is durable, provides good signal quality, and is easy to embed. The electrodes are connected to an ECG display. The display can also include the oxygen saturation readings from the pulse oximeter and the blood pressure readings from the blood pressure cuff.

There are many instances when the present invention will provide sufficient patient monitoring. As noted above, one example would be in what are known as minor procedures. In the aggregate, given the tens of millions of such procedures annually and the premium placed on physician, nursing, and staff time, the savings in time, complexity, potential problems, and cost would be substantial.

The costs associated with implementing the present invention should be moderate and non-recurring. As ECG monitors are retired, monitors with this new system can be swapped in. The ECG circuitry for the original ECG inputs and the new inputs from the pulse oximeter and BP cuff are shared, except for the circuitry correcting the polarity of the new system. Importantly, such a system requires no change of technique on behalf of the medical practitioner.

Other uses and advantages of the present invention will become apparent from the drawings and detailed description below.

DETAILED DESCRIPTION OF THE PREFERRED EMBODIMENTS

Figure 1:
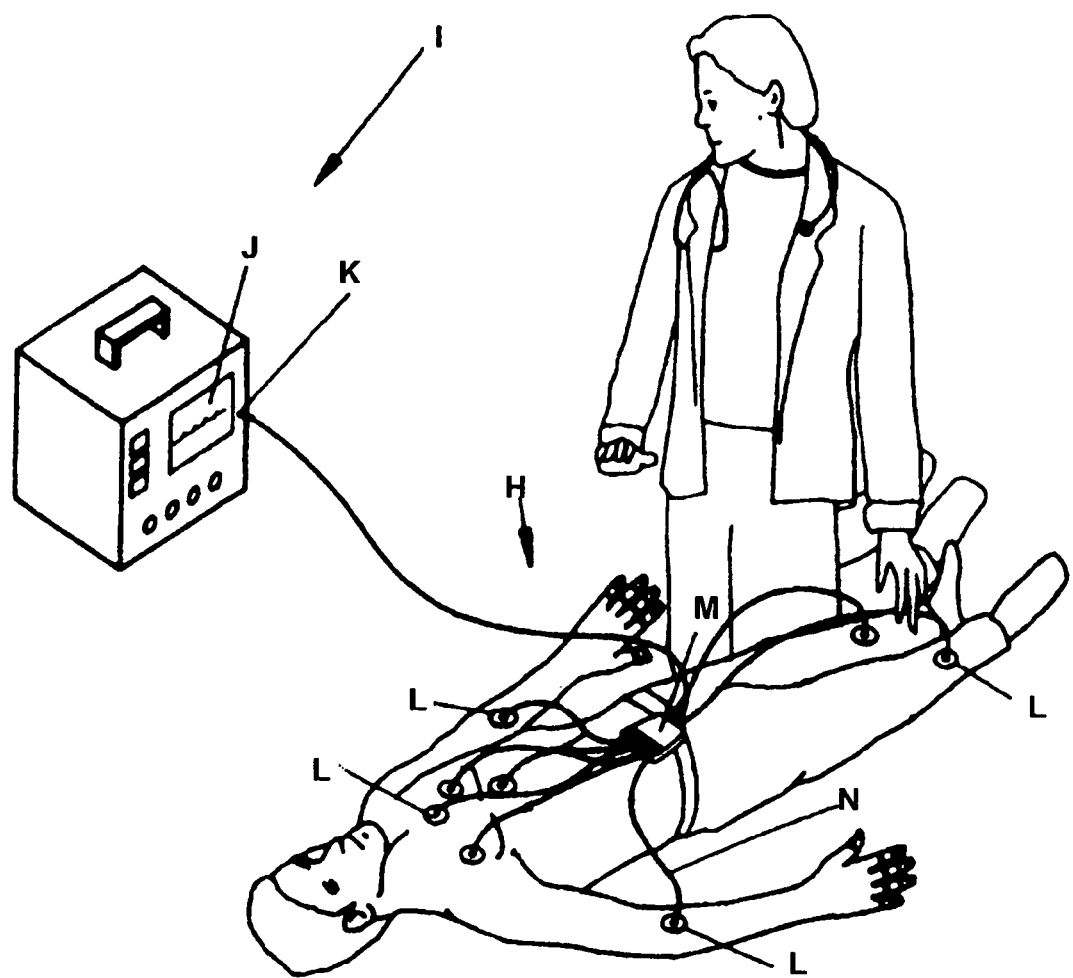
FIG. 1 shows a patient being monitored with a prior art ECG display monitor, harness, wires, and disposable electrodes.

FIG. 1 depicts a patient H being monitored with a prior art ECG monitor I showing display J. The cord K connects to harness hub M that receives wires N that connect to disposable electrodes L. As depicted, the display J of prior art monitor I displays an ECG tracing or waveform.

Figure 2:
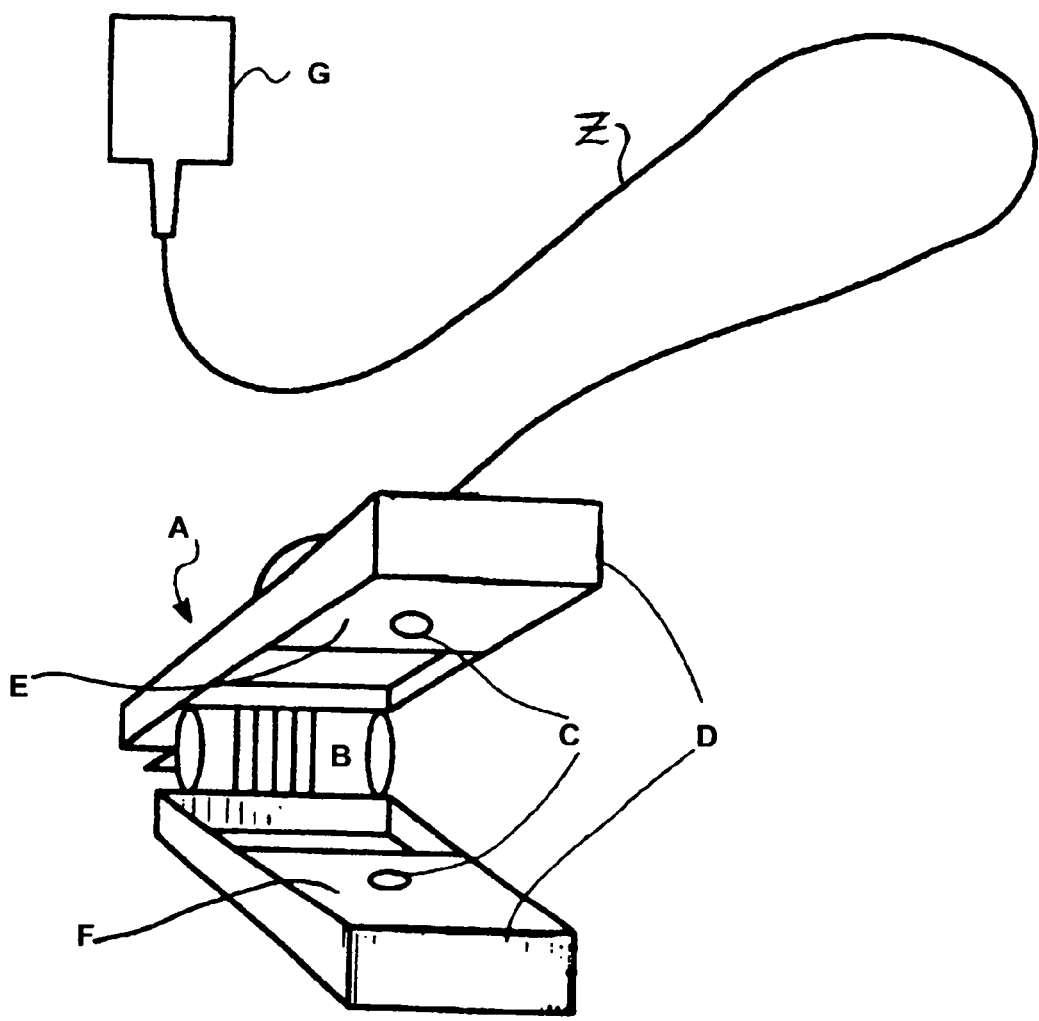
FIG. 2 depicts a pulse oximeter probe A configured to include one active ECG electrode E and one ground ECG electrode F.

In FIG. 2, a prior art pulse oximeter probe A has been modified by having the inner surfaces of finger pads D function as electrodes E and F. The electrodes E and F are an active wire and a ground wire respectively, and are electrically connected to plug G by incorporating two dedicated wires within the pulse oximeter cable. The spring mechanism B, LED and photodiode windows C, probe finger pads D, and connector G can be standard, prior art components. In prior art monitoring systems, a pulse oximeter A, without the modifications of the present invention, is often connected (not shown) by a connector G to monitor I to display an oxygen saturation level. This connection is typically separate from the connection K in FIG. 1. A single prior art display J will often simultaneously or sequentially show both the ECG tracing and the oxygen saturation level determined by the pulse oximeter.

For the present invention, it is preferable to include electrodes as a reusable part of the interior of the pulse oximeter A, although another embodiment could use disposable electrodes that connect to a wire lead in the oximeter that would provide an ECG signal to the display. The preferred embodiment of the present invention utilizes dry reusable electrodes embedded within the BP cuff S and pulse oximeter probe A. It is found that dry electrodes manufactured from Ag/AgCl provide a signal quality comparable to disposable, gel-mounted electrodes. The sintered Ag/AgCl coating can be applied over a flexible matrix such as a wire mesh or carbon fiber matrix to form the finger pads E and F. By using an Ag/AgCl sintered coating and electrically connecting connector G to the ECG monitor, an excellent ECG signal is generated. The signal quality results from the large surface area of the probes and the spring B which firmly applies the electrodes and lowers resistance to current flow. Interestingly, it is also recognized that Ag/AgCl has inherent bactericidal properties that will decrease surface contamination, as the blood pressure cuffs and pulse oximeter finger probes most utilized are not disposable. The cuffs and oximeters used in connection with the present invention can also be disinfected by the various known methods typically used in a medical environment.

In one embodiment of the invention, the pulse oximeter and blood pressure cuff are both used to produce a single ECG tracing. In practice, this is possible due to the consistent placement by the medical practitioner of the BP cuff S and pulse oximeter probe A on separate arms. Thus, in FIG. 2, wire Z and connector G could transfer information concerning the oxygen saturation and cardiac function to a monitor like monitor I in FIG. 1.

Figure 3:
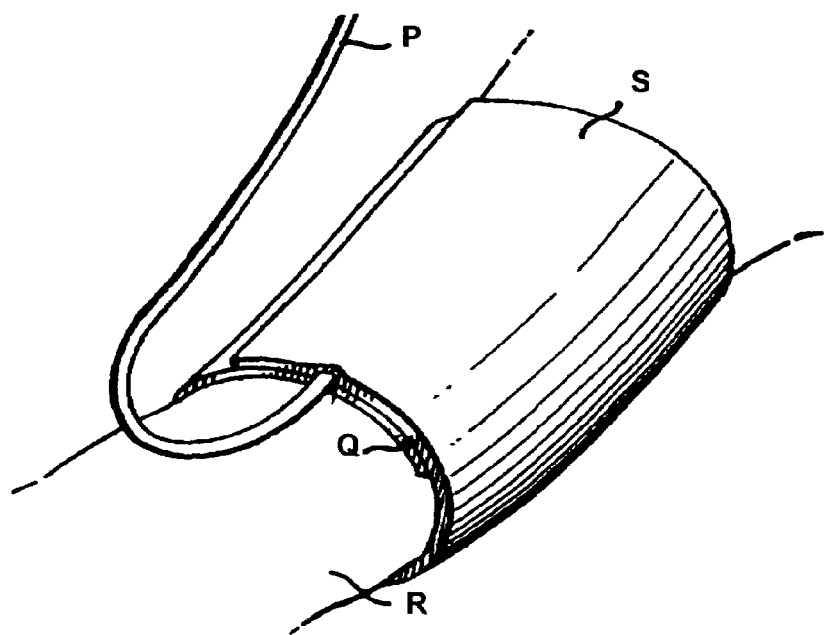
FIG. 3 shows a prior art blood pressure cuff S that can be configured to input an ECG lead into the display.
Figure 4:
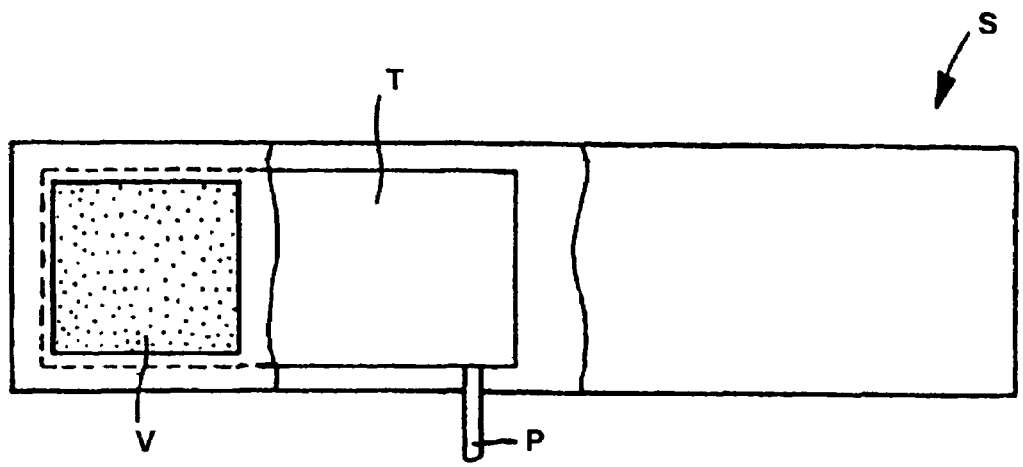
FIG. 4 shows the inner surface of the blood pressure cuff S of FIG. 3, modified to provide an ECG lead.

FIG. 3 depicts a prior art blood pressure cuff S, secured to a patient's arm R, with a Velcro fastener Q. The cuff S can be modified to include an active ECG lead. FIG. 4 shows a modified version of the inner surface of the blood pressure cuff S of FIG. 3. Active electrode V is positioned partially adjacent to inflation bladder T that connects via tubing P to a "vital signs" monitor such as monitor I in FIG. 1. Electrode V is electrically coupled to this "vital signs" monitor via a concealed wire (not shown) in tube P that connects to the monitor via a metallic pneumatic coupling (not shown) that now also functions as an electrical coupler. In the present invention, the electrode size, large surface area, and Velcro fastener ensure that there is adequate coupling of the electrode to the skin. It is desirable to provide as much electrode contact to the patient's arm as possible.

Other possible arrangements of one or more electrodes coupling the surface of the blood pressure cuff to the ECG monitor are possible, and will be understood by those of skill in the art. In FIG. 4, the pressure wave transfer necessary for oscillometric determination of blood pressure is not affected by the electrode, because the electrode surface area is located adjacent to the bladder. Another embodiment could use a long electrode wire thin enough that pressure waves are not dampened, so that the determination of an ECG waveform and the measurement of blood pressure do not interfere with each other.

By using the pulse oximeter and blood pressure cuff to provide two active electrodes and a ground, sufficient electrical input is obtained to generate a high quality ECG tracing. Convention defines the left arm as the positive electrode generating a generally positive and characteristic ECG tracing. In some instances the ECG polarity may be reversed if the BP cuff and pulse oximeter are placed on the wrong arms. Those of skill in the art will understand this potential problem and will appreciate a variety of ways to return the display to a standard polarity. One solution would be to modify the signal processing hardware and/or software so that a standard lead 1 polarity will be displayed automatically. Such a modification could include pattern detection logic to determine whether to invert the signal prior to display. Such logic could be provided through either hardware logic circuitry or through software, or both, as those of skill in the art will appreciate. Then, the ECG monitor would read out a standard lead 1 ECG tracing (or some other lead, if the device is so configured), regardless of the orientation of BP cuff and pulse oximeter.

Other electrode and lead arrangements are possible. In one example, a modified pulse oximeter probe containing an active and ground electrode could be utilized in conjunction with a single disposable electrode and wire to form a working lead. In a second example, the blood pressure cuff could be configured to have an active and ground electrode.

This system is designed to work in conjunction with the current systems and methods of ECG monitoring. For example, a medical practitioner may want to intraoperatively use the current system of multiple wires and disposable electrodes for purposes of sequentially monitoring different ECG leads. When the input to the ECG monitor is from the prior art wire harness, this will be the primary input and will be displayed. After an uneventful surgery and anesthetic, the patient is brought to the recovery room and the patient's ECG is then monitored by the combination of the BP cuff and pulse oximeter described in the present invention. The configuration used in the recovery room would constitute a secondary input and display of the ECG tracing. It could be displayed only when the primary input is absent.

In addition, the system can be configured so the inputs would not be mutually exclusive. For example, should a disposable electrode for the primary input become dislodged during monitoring, and should a secondary input (from the pulse oximeter and BP cuff) be able to complete the missing input necessary for an ECG tracing, the combination of the primary and secondary inputs could be utilized to display a constant ECG without disruption or the need to reapply the disposable electrode. Adapting the current ECG signal processing and display functions could be accomplished by one of ordinary skill in the art. A medical practitioner may wish to utilize a dual electrode pulse oximeter probe on the right hand with a single disposable probe on the left chest wall resulting in a lead two readout. The ECG monitor can be configured to display the ECG waveform in a variety of ways such as a printed display on paper or on a typical electronic display, whether CRT, LCD, or on some other well known device. Primary, secondary, and/or combined leads could also be depicted and differentiated on paper or on the electronic display through a variety of methods, whether textual, graphic, or by color.

As ECG monitors are retired, monitors with this dual input system can be swapped in. The ECG circuitry for the primary and secondary inputs is shared except for the circuitry correcting the polarity of the secondary system. Importantly, such a system requires no change of technique on behalf of the medical practitioner.

Numerous variations and embodiments of the present invention are envisioned. While the preferred embodiment of the invention includes a simultaneous electronic display of ECG, BP, and oxygen saturation level on one screen, it would be possible to have individual LCDs on the pulse oximeter and BP cuff that displayed each device's respective reading. The electronic screen (and/or printer) associated with the monitor could display just the waveform tracing or some combination of the tracing and the other patient monitoring information. Similar, it is expected that a preferred commercial embodiment of the invention would include the capacity to process the prior art wire harness input plus the ECG capability associated with a pulse oximeter and/or BP cuff modified to generate an ECG tracing. Such a configuration would provide for maximum flexibility in equipment use. Nevertheless, the present invention could also be configured as an inexpensive, stand-alone monitoring device. In other words, the monitoring system would use inputs just from the pulse oximeter and/or BP cuff, which would also provide a single ECG tracing. There would be no provision for additional inputs for more detailed ECG information.

Therefore, it will be understood by those of skill in the art that changes may be made to the present invention, and that changes in its use may also be made, without departing from the spirit of the invention, which is defined in the following claims.

What is claimed is:

1. In an ECG patient monitoring system with an ECG tracing display, the improvement consisting essentially of:
   a single blood pressure cuff;
   a single pulse oximeter;
   a single ECG lead consisting of a Lead I with a signal that is generated by;
   a first electrical connection operatively connected to the ECG monitoring system and to one electrode located on an inner side of the pulse oximeter for operative contact with a patient's skin on one of the right and left arm or hand;

a second electrical connection operatively connected to the ECG monitoring system and to one electrode on the an inner side of the blood pressure cuff for operative contact with the patient's skin on the other of the right and left arm to create the ECG Lead I; and an electrical ground.

2. The invention of claim 1, wherein the electrodes are dry electrodes comprising a sintered coating of Ag/AgCl.

3. The invention of claim 1, wherein the electrical ground includes an electrode located on the inner side of the blood pressure cuff.

4. The monitoring system of claim 3, further including at least one of hardware and software polarity detection logic.

5. The monitoring system of claim 1, wherein the electrical ground includes an electrode located on the inner side of the pulse oximeter.

6. The monitoring system of claim 5, further including at least one of hardware and software polarity detection logic.

7. A system for monitoring a patient's oxygen saturation level, blood pressure, and cardiac function described by a Lead I ECG tracing, consisting essentially of:
- an ECG monitoring system with at least one ECG display;
- a single blood pressure cuff with an inner and outer surface, adapted to be mounted on one of the right and left side of the patient and connected to at least one blood pressure display;
- a single pulse oximeter with an inner and outer surface, adapted to be mounted on the other of the right and left side of the patient and connected to at least one oxygen saturation display;
- a first ECG electrode located on the inner surface of the pulse oximeter and operatively connected to the ECG monitoring system;
- a second ECG electrode located on the inner surface of the blood pressure cuff and operatively connected to the ECG monitoring system;
- a ground electrode mounted on the inner surface of the blood pressure cuff and operatively connected to an electrical ground; and
- wherein the electrical potential across the ECG electrodes and the ECG monitoring system generate an ECG Lead I.

8. The monitoring system of claim 7, wherein the ECG display, the oxygen saturation display, and the blood pressure displays comprise at least one unitary display of the ECG tracing, the oxygen saturation level, and the blood pressure.

9. The monitoring system of claim 7, wherein the ECG electrode connected to the pulse oximeter is an integral part of the pulse oximeter.

10. The monitoring system of claim 9, wherein the ECG electrode is comprised of a sintered coating of Ag/AgCl.

11. The monitoring system of claim 10, wherein all of the ECG electrodes are comprised of a sintered coating of Ag/AgCl.

12. The monitoring system of claim 11, wherein the ECG electrode connected to the blood pressure cuff is an integral part of the blood pressure cuff.

13. The monitoring system of claim 12, further comprising at least one of hardware and software polarity detection logic.

14. The monitoring system of claim 7, wherein the ECG electrodes are removably affixed to the inner surfaces of the pulse oximeter and blood pressure cuff.

15. The monitoring system of claim 14, wherein all the electrodes are comprised of a sintered coating of Ag/AgCl.

16. The monitoring system of claim 7, wherein the ground electrode is located on the inner surface of the pulse oximeter.

* * * * *